Sept. 13, 1949. P. R. PARSON Plant Pat. 872

PRUNE TREE

Filed Sept. 12, 1947

INVENTOR
Peter R. Parson

By
H. Geiler,
Attorney

Patented Sept. 13, 1949

Plant Pat. 872

UNITED STATES PATENT OFFICE

872

PRUNE TREE

Peter R. Parson, Forest Grove, Oreg.

Application September 12, 1947, Serial No. 773,585

1 Claim. (Cl. 47—62)

The fruit of this tree is about the same size and color as a good Italian prune, although it is slightly more pointed than the ordinary Italian prune. It is a free-stone prune with an unusually small seed.

One of the main distinctions between the fruit of this tree and the ordinary Italian prunes grown by me in the same locality is the fact that this prune is invariably much sweeter. A careful laboratory analysis has shown that this prune averages 50.7 percent sugar content whereas the average for ordinary Italian prunes from the same locality is 41.0 percent sugar content.

Another characteristic of this prune tree is that the tree is hardier than other Italian prune trees, better able to withstand unfavorable weather conditions, and heavier bearing. During the past two years, this prune tree has averaged two bushels of prunes per tree, while the average crop from my orchard of ordinary Italian prune trees during the same period was three-fourths of a bushel per tree.

The blossoms of this tree are easily distinguished from the blossoms of the ordinary Italian prune tree. The blossoms of this tree appear from one week to ten days earlier than on ordinary Italian prune trees, and come two to a bud instead of in clusters, and are more evenly distributed over the entire branch. The blossoms are whiter and the petals thicker, heavier and whiter, and the blossoms appear in greater number than on ordinary Italian prune trees. This difference is very noticeable especially when a group of these trees appears next to a group of ordinary Italian prune trees, and this difference can be distinguished from quite a distance.

The leaf resembles the leaf of an ordinary Italian prune tree except that it is slightly less pointed and has a tendency to be slightly lighter in color.

The accompanying illustrations have been reproduced from Kodachrome films made from the blossoms, when the trees were in bloom, and made from the leaves and fruit, when the fruit was ripe. In these illustrations, constituting true color reproductions:

Figure 1:
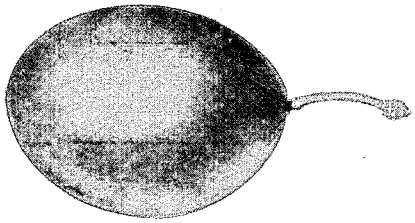
Fig. 1 shows the fruit itself.
Figure 2:
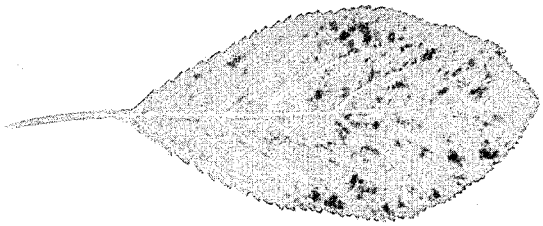
Fig. 2 shows the prune leaf.
Figure 3:
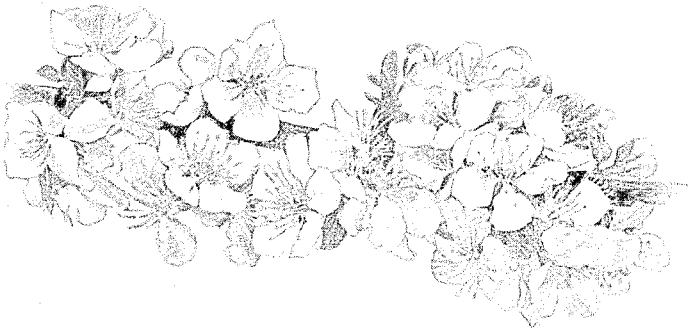
Fig. 3 shows a portion of a branch with the blossoms appearing thereon.

An additional characteristic of this new prune tree is that the blossoms and fruit will appear on new wood on the tree after the first year. On all other Italian prune trees with which I have had any experience the blossoms and fruit do not appear on the new wood until after the second year.

This new prune tree originated with a seedling grown near Forest Grove, Oregon, and my attention was called to this original tree by the unusual characteristics of its prunes several years ago. At that time the prunes from this seedling, together with the prunes from the other trees in the same and adjacent orchards were delivered to me for drying. Upon making tests of the dried prunes, I was immediately impressed with the difference between the prunes from this particular tree and the prunes from the other trees, and thereupon for the next two years I watched this tree carefully and verified the continuance of the distinguishing features mentioned above. I then proceeded to propagate the tree by cutting buds from it and grafting these buds on plum, prune and peach seedlings. I continued this propagation for a period of five years, carefully watching and observing the propagated trees. The first budded trees began satisfactory bearing at the age of two years and showed continued increase in bearing at three and at four years. I have now propagated a sufficiently large number of these trees in this manner to verify that the same characteristics will hold true with every tree thus propagated. I have also propagated the trees sasisfactorily by cutting and grafting, but I believe the best and surest method of propagation is by grafting a bud taken from a tree reproduced by bud and traceable back to the original tree. All the trees which I have propagated are uniformly heavy bearers and have proved that they were able to withstand the unfavorable weather conditions of the past year more satisfactorily than the other prune trees in that locality. The propagation which I have made has continuously produced fruit exactly the same as that of the original tree. The fruit ripens from one week to ten days earlier than on other Italian prune trees.

The dried prunes of these trees, due chiefly to their high sugar content, have proven to be superior for packing, shipping, storage, canning and eating than dried prunes from the other Italian prune trees grown in this same section of the country.

In the above description the term "Italian prune" is to be understood as referring to the ordinary Italian prune as distinguished from such types of prunes as the "date prune,"

"petite prune," and "Santa Clara prune," which should not be classified as Italian prunes.

I claim:

A new variety of prune tree as described, the tree and fruit resembling that of the Italian prune but characterized in that the fruit has a higher sugar content and ripens earlier than the Italian prune, that the tree is hardier and heavier bearing than the tree of the Italian prune, that the blossoms are thicker, whiter, more evenly distributed over the branches and appear earlier than the blossoms on the Italian prune tree, and that blossoms and fruit will appear on new wood on the tree after the first year.

PETER R. PARSON.

No references cited.